US008153383B2

(12) United States Patent
Collins et al.

(10) Patent No.: US 8,153,383 B2
(45) Date of Patent: Apr. 10, 2012

(54) **MYCOBACTERIAL CULTURE SCREENING TEST FOR *MYCOBACTERIUM AVIUM* COMPLEX BACTERIA**

(75) Inventors: Michael T. Collins, Blue Mounds, WI (US); Sung Jae Shin, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 232 days.

(21) Appl. No.: 12/406,253

(22) Filed: Mar. 18, 2009

(65) Prior Publication Data

US 2009/0305302 A1 Dec. 10, 2009

Related U.S. Application Data

(60) Provisional application No. 61/037,665, filed on Mar. 18, 2008, provisional application No. 61/038,288, filed on Mar. 20, 2008.

(51) Int. Cl.
*G01N 33/00* (2006.01)
*G01N 33/53* (2006.01)
*G01N 33/554* (2006.01)

(52) U.S. Cl. ......... 435/7.1; 435/7.2; 435/7.32; 435/7.92

(58) Field of Classification Search ........................ None
See application file for complete search history.

(56) References Cited

U.S. PATENT DOCUMENTS

| | | | |
|---|---|---|---|
| 3,791,932 | A | 2/1974 | Schuurs et al. |
| 3,875,011 | A | 4/1975 | Rubenstein et al. |
| 3,879,262 | A | 4/1975 | Schuurs et al. |
| 4,256,834 | A | 3/1981 | Zuk et al. |
| 4,261,968 | A | 4/1981 | Ullman et al. |
| 4,490,473 | A | 12/1984 | Brunhouse |
| 6,221,364 | B1 | 4/2001 | Pavelka, Jr. et al. |

FOREIGN PATENT DOCUMENTS

| | | |
|---|---|---|
| EP | 1780547 A1 | 5/2007 |
| WO | WO 97/34149 | 9/1997 |
| WO | WO 2008/030865 | 3/2008 |

OTHER PUBLICATIONS

Cho, et al., Proteomic Identification of Immunogenic *Mycobacterium paratuberculosis* Proteins, Eighth International Colloquium on *paratuberculosis*, Copenhagen, Denmark, Aug. 14-17, 2005, MT XP002464448 [Abstract].
Cho, et al., Identification of Proteins of Potential Diagnostic Value for Bovine *paratuberculosis*, Proteomics 6 (21):5785-5794, Oct. 2006.
Cho, et al., Comparison of the Proteosomes and Antigenicities of Secreted and Cellular Proteins Produced by *Mycobacterium paratuberculosis*, Clin. Vaccine Immunol. 13(10):1155-1161, Oct. 2006.
Gardner, et al., Receiver-operating Characteristic Curves and Likelihood Ratios: Improvements Over Traditional Methods for the Evaluation and Application of Veterinary Clinical Pathology Tests, Vet. Clin. Pathol. 35(1):8-17, 2006.
Kaufman, et al., Handbook of Molecular and Cellular Methods in Biology and Medicine, CRC Press, Boca Raton, FL, 1995.
Miller, A Short Course in Bacterial Genetics, Cold Spring Harbor Laboratory Press, Cold Spring Harbor, NY, 1992.
Sambrook, et al., Molecular Cloning: A Laboratory Manual, 3rd ed., Cold Spring Harbor Laboratory Press, Cold Spring Harbor, NY, 2001.
Singer, et al., Genes and Genomes: A Changing Perspective, University Science Books, Mills Valley, CA, 1991.
Sung, et al., Possible Association of GroES and Antigen 85 Proteins with Heat Resistance of *Mycobacterium paratuberculosis*, Appl. Environ. Microbiol. 70(3):1688-1697, 2004.
Sweeney, et al., Longitudinal Study of ELISA Seroreactivity to *Mycobacterium avium* Subsp. *paratuberculosis* in Infected Cattle and Culture-Negative Herd Mates, J. Vet. Diagn. Invest. 18:2-6, 2006.
PCT International Preliminary Report on Patentability, PCT/US2007/077625, Mar. 19, 2009.
United States Patent and Trademark Office, Office Action Summary and Detailed Action, U.S. Appl. No. 11/850,282, Jun. 24, 2008.
Response to Restriction/Election Requirement, U.S. Appl. No. 11/850,282, Jul. 24, 2008.
United States Patent and Trademark Office, Office Action Summary and Detailed Action, U.S. Appl. No. 11/850,282, Sep. 19, 2008.
Amendment and Request for Reconsideration, U.S. Appl. No. 11/850,282, Jan. 7, 2009.
United States Patent and Trademark Office, Office Action Summary and Detailed Action, U.S. Appl. No. 11/850,282, Apr. 30, 2009.
Amendment and Request for Reconsideration, U.S. Appl. No. 11/850,282, Jun. 30, 2009.
United States Patent and Trademark Office, Interview Summary, U.S. Appl. No. 11/850,282, Jul. 1, 2009.
United States Patent and Trademark Office, Office Action Summary and Detailed Action, U.S. Appl. No. 11/850,282, Jul. 10, 2009.
Amendment and Request for Reconsideration, U.S. Appl. No. 11/850,282, Oct. 12, 2009.
United States Patent and Trademark Office, Office Action Summary and Detailed Action, U.S. Appl. No. 11/850,282, Jan. 22, 2010.
Amendment in Response to Final Office Action, U.S. Appl. No. 11/850,282, Mar. 22, 2010.
United States Patent and Trademark Office, Office Action Summary and Detailed Action, U.S. Appl. No. 11/850,282, Apr. 5, 2010.
United States Patent and Trademark Office, Office Action Summary and Detailed Action, U.S. Appl. No. 11/850,282, May 17, 2010.
United States Patent and Trademark Office, Interview Summary, U.S. Appl. No. 11/850,282, Oct. 13, 2010.

(Continued)

*Primary Examiner* — Albert Navarro
(74) *Attorney, Agent, or Firm* — Quarles & Brady, LLP

(57) ABSTRACT

A method of antigen-capture assays that uses the detection of antigens secreted into liquid culture is provided. Also provided are antibodies to *Mycobacterium avium* complex-specific antigens, and diagnostic kits and systems for the detection of the presence of mycobacteria in liquid samples.

9 Claims, 11 Drawing Sheets

OTHER PUBLICATIONS

Response to Non-Final Office Action, U.S. Appl. No. 11/850,282, Oct. 14, 2010.
United States Patent and Trademark Office, Office Action Summary and Detailed Action, U.S. Appl. No. 11/850,282, Nov. 2, 2010.
Intellectual Property Office of New Zealand, Examination Report, Patent Application No. 575023, Jun. 30, 2010.
Choudhry and Saxena, "Detection of *Mycobacterium tuberculosis* Antigens in Urinary Proteins of Tuberculosis Patients," *Eur. J. Clin. Microbiol Infect Dis.*, 21:1-5 (2002).
Collins et al., "Evaluation of Five Antibody Detection Tests for Diagnosis of Bovine *paratuberculosis*," *Clinical and Diagnostic Laboratory Immunology*, 12(6):685-292 (2005).
Glickman et al., "Rapid Identification of Mycolic Acid Patterns of Mycobacteria by High-Performance Liquid Chromatography Using Pattern Recognition Software and a *Mycobacterium* Library," *J. Clin. Microbiol.*, 32(3):740-745 (1994).
Greenwood et al., "The Preparation of $^{131}$I-Labelled Human Growth Hormone of High Specific Radioactivity," *Biochem. J.*, 89:114-123 (1963).
Harlow and Lane, *Labeling Antibodies with Iodine*, Cold Spring Harbor Protocols, 18:pdb.prot4287 (2006).
Pereira et al., "Development of Antigen Detection Assay for Diagnosis of Tuberculosis Using Sputum Samples," *Journal of Clinical Microbiology*, 38(6):2278-2283 (2000).
Shin et al., "Diagnosis of Bovine *paratuberculosis* by a Novel Enzyme-Linked Immunosorbent Assay Based on Early Secreted Antigens of *Mycobacterium avium* subsp. *paratuberculosis*," *Clin. Vaccine Immunol.*, 15(8):1277-1281 (2008).
Shin et al., Rapid Mycobacterial Liquid Culture-Screening Method for *Mycobacterium avium* Complex Based on Secreted Antigen-Capture Enzyme-Linked Immunosorbent Assay, *Clinical and Vaccine Immunology*, 16(5):613-620 (2009).
Sung and Collins, "Variation in Resistance of *Mycobacterium paratuberculosis* to Acid Environments as a Function of Culture Medium," *Appl. Environ. Microbiol.*, 69(11):6833-6840 (2003).
International Search Report dated Jul. 15, 2009 received in corresponding PCT Application No. PCT/US2009/037469.
Hughes et al., "Proteomic comparison of *Mycobacterium avium* subspecies *paratuberculosis* grown in vitro and isolated from clinical cases of ovine *paratuberculosis*," Microbiol. 153:196-205 (2007).
Rastogi et al., "The mycobacteria: an introduction to nomenclature and pathogenesis," Rev. Sci. Tech. Off. Int. Epiz. 20: 21-54 (2001).
Turenne et al., "*Mycobacterium avium* in the postgenomic era," Clin. Microbiol. Rev. 20:205-229 (2007).

MYCOBACTERIAL CULTURE SCREENING TEST FOR *MYCOBACTERIUM AVIUM* COMPLEX BACTERIA

CROSS-REFERENCE TO RELATED APPLICATIONS

This invention claims priority to U.S. Provisional Patent Application Ser. Nos. 61/037,665, filed Mar. 18, 2008, and 61/038,288, filed Mar. 20, 2008, both of which are herein incorporated by reference.

FIELD OF THE INVENTION

This invention relates to the field of diagnostic assays for detecting the presence of mycobacteria.

BACKGROUND

Members of the *Mycobacterium avium* complex (MAC) are a family of intracellular bacterial pathogens causing significant disease in both animals and humans. The complex contains four subspecies of *M. avium: M. avium* subsp. *avium* (MAA), *M. avium* subsp. *paratuberculosis* (MAP), *M. avium* subsp. *hominissuis* (MAH), and *M. avium* subsp. *silvaticum* (MAS). *Mycobacterium intracellulare* is also a member of the complex.

The most common method for diagnosis of mycobacterial infections in humans and animals begins with growth (isolation) of the causative organism in liquid culture media. While direct detection technology (such as PCR) can be done on clinical samples, most studies find trying to find the bacteria's DNA less sensitive than culture-based methods. Also, culture yields the pathogens needed for subsequent testing such as antibiotic susceptibility or molecular epidemiology. The success of culture-based methods for mycobacteria depends heavily on specimen processing techniques that eliminate non-mycobacterial microflora from the sample. The tubes of inoculated liquid media are monitored by instruments that incubate and "examine" the culture for evidence of microbial growth using indicators such as oxygen consumption or gas pressure inside the sealed culture vessel. Examples of these diagnostic systems are the BACTEC MGIT 960 system (BD Diagnostic Systems, Franklin Lakes, N.J.), and Trek ESP II system (Trek Diagnostic Systems, Cleveland, Ohio). These instruments generally handle 300-1,000 cultures at a time and cost in excess of $50,000. The culture media associated with each instrument retails for $5 to $10 per sample tube depending on instrument lease agreements and volume discounts.

After an instrument signals that microbial growth is occurring in the culture tube, a variety of assays must be performed to identify the micro-organism(s) in the tube that triggered the signal. Such assays vary in sensitivity, specificity, and cost. Possible outcomes of mycobacteria identification assays on isolates from liquid cultures include: 1) false-signal by the instrument, i.e. no microorganisms were detected, 2) identification of a mycobacterial pathogen of limited clinical significance, e.g. a non-pathogenic environmental *Mycobacterium* sp., or 3) identification of a mycobacterial pathogen of importance.

The vast majority of clinically important mycobacterial pathogens generally fall into two groups: *Mycobacterium tuberculosis* Complex (MTBC) and the *Mycobacterium avium* complex (MAC). *Mycobacterium leprae*, the cause of leprosy, is also an important mycobacterial pathogen but it is far less common and is presently not cultivable in vitro. In developing countries MTBC is the predominant mycobacterial pathogen of concern. In developed countries MAC pathogens are more common, particularly in immunocompromised patients such as people with HIV or under treatment for cancer.

Typically, definitive identification of mycobacterial pathogens isolated from culture is primarily based on PCR. The PCR assays differ in design from those used for direct pathogen detection in clinical samples and are marketed specifically for mycobacterial identification from cultures. An example of one of the leading products in this market is AccuProbe® (Gen-Probe, San Diego, Calif.). Most such assays are target pathogen DNA-specific and rule in/out a specific pathogen group, e.g. MTBC or MAC. If the assay is positive, the result is reported as, for example, MAC complex positive. The specific species of mycobacteria within the complex is usually not determined. If the PCR assay is negative, other PCRs may be required to arrive at a diagnosis. The PCR assays may be costly and laborious.

A positive signal appears in automated liquid culture systems used for mycobacteria isolation when growth of a microorganism triggers the system's sensor. Rapid, low-cost methods are therefore desired to weed out diagnostically irrelevant cultures that can be signal-positive due to non-mycobacterial organisms. The present invention provides compositions and methods for achieving these and related objectives.

BRIEF SUMMARY

Provided are compositions and methods for the detection of mycobacteria growing in liquid samples. Also provided are novel antigen and antibody preparations, kits, systems, and methods that can be used in assays for detecting the presence of *Mycobacterium avium* complex bacteria.

Methods of detecting the presence of mycobacteria in liquid cultures are provided. The methods include the steps of: providing capture antibodies obtained from a subject immunized with mycobacteria-secreted antigens; contacting the liquid culture with the capture antibodies; providing detection antibodies obtained from a subject immunized with the mycobacteria-secreted antigens; and detecting the presence of antigen-bound detection antibodies in the liquid culture to indicate the presence of the mycobacteria in the liquid culture. The detected mycobacteria may include *Mycobacterium avium* complex.

The methods may include absorbing nonspecific antibodies using heterologous antigens, where absorption is performed prior to contacting the capture antibody and the detection antibody with the liquid culture. In the practice of the methods, both antibodies may be specific for one or more *Mycobacterium avium* complex secreted antigens. In some embodiments, the heterologous antigens may be from *M. phlei*, other mycobacteria, or *E. coli*. In the practice of the methods, detection of the presence of antigen-bound detection antibodies in the liquid culture may include using an enzyme-linked immunosorbent assay (ELISA). The capture antibodies may be affixed to solid support. In some embodiments, the capture antibody may be produced in chickens, and the detection antibodies may be produced in rabbits.

In the practice of the methods, the detection antibodies may be labeled. The detection antibodies may be conjugated to enzymes. Preferably a conjugate such as anti-rabbit Ig conjugated to an enzyme may be used to determine that the detection antibody has bound to *Mycobacterium avium* complex antigens captured in the assay. The methods may employ any conjugate capable of reacting with bound *Mycobacterium avium* complex antigen detection antibody.

Systems for the detection of the presence of mycobacterial pathogens in liquid cultures are provided. The systems include: capture antibodies obtained from subjects immunized with a *Mycobacterium*-secreted antigens; and detection antibodies obtained from a subject immunized with the *Mycobacterium*-secreted antigens. The mycobacterial pathogens may be *Mycobacterium avium* complex. In the systems, the capture antibodies may be chicken anti-*Mycobacterium avium* complex antibodies, and the detection antibodies may be rabbit anti-*Mycobacterium avium* complex antibodies.

The capture antibodies may be affixed to solid support. The detection antibodies may be labeled. The detection antibodies may be conjugated to enzymes. The systems may further include an absorbing antigen preparation. The absorbing antigen preparation may include heterologous antigens. The absorbing antigen preparation may include heterologous antigens from *M. phlei* or *E. coli*.

DETAILED DESCRIPTION OF THE PRESENTLY PREFERRED EMBODIMENTS

Figure 1:
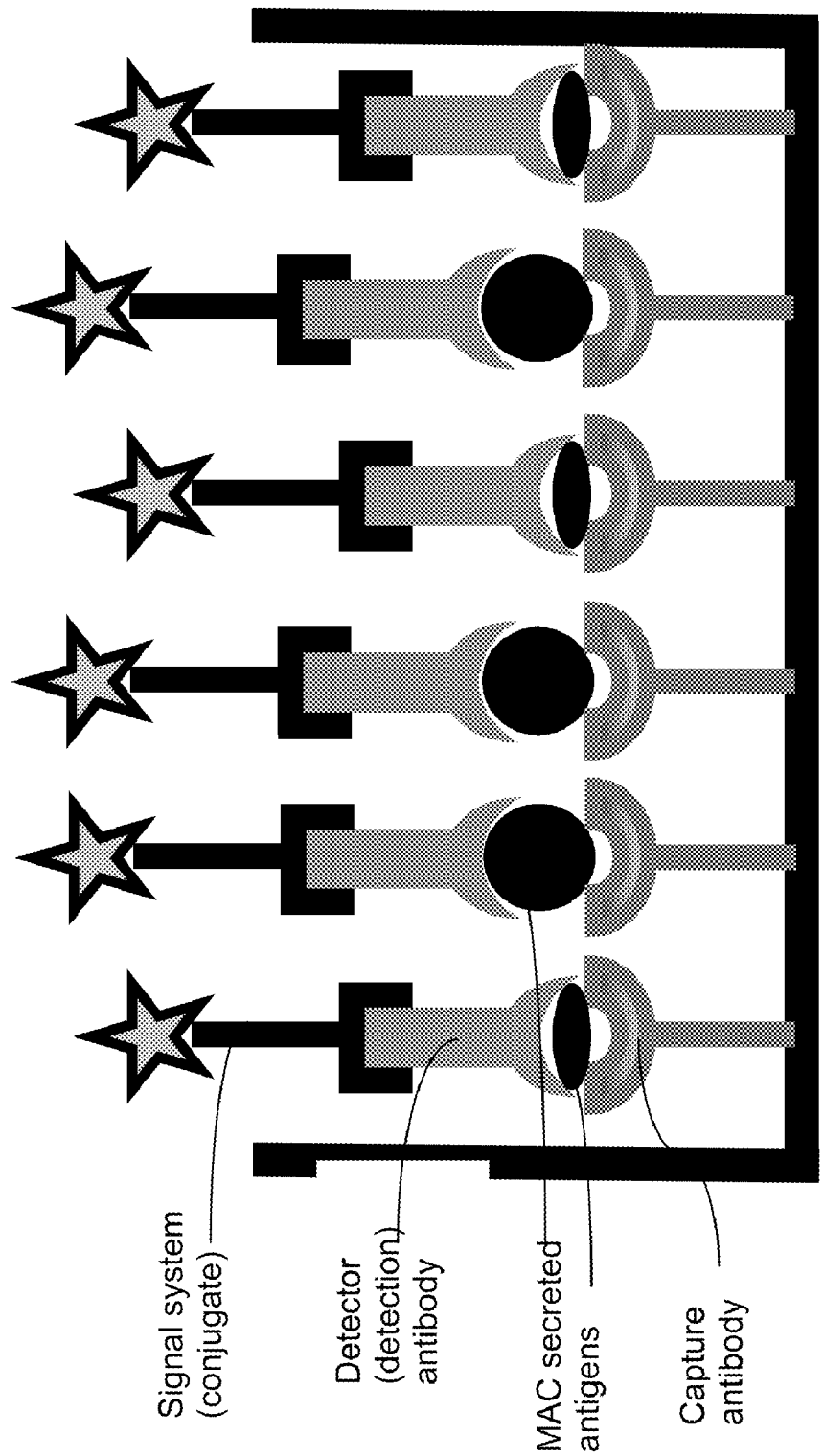
FIG. 1 is a schematic outline of one embodiment of the present invention.

"*Mycobacterium avium* complex" (MAC) is a group of genetically-related bacteria belonging to the genus *Mycobacterium*. It includes *Mycobacterium avium* subspecies *avium* (MAA), *Mycobacterium avium* subspecies *hominissuis* (MAH), and *Mycobacterium avium* subspecies *paratuberculosis* (MAP). Historically, MAC has also included *Mycobacterium intracellulare* (MI)—a distinct species of bacteria. The present invention specifically contemplates Ml as being included in MAC.

"Antigen" is a substance that evokes an immune response in a subject, especially the production of antibodies. Antigens are usually proteins or polysaccharides foreign to the subject, but may also be any type of molecule, including small molecules (haptens) coupled to a carrier-protein. For example, a *M. paratuberculosis* antigen is a substance that evokes an anti-*M. paratuberculosis* response in a subject, when the subject is immunized with that antigen.

"Antigenic preparation" is a preparation that includes antigens.

"Antibody" is used in the broadest sense and specifically covers paratuberculosis-specific monoclonal antibodies (including agonist, antagonist, and neutralizing antibodies), paratuberculosis-specific antibody compositions with polyepitopic specificity, single chain paratuberculosis-specific antibodies, and fragments of paratuberculosis-specific antibodies. The antibodies may be anti-*M. avium* monoclonal or polyclonal antibodies per se, immunologically effective fragments thereof (e.g., $F_{ab}$, $F_{ab'}$, or $F_{(ab')2}$), or a single chain version of the antibodies, usually designated as $F_v$ regions. Methods of producing polyclonal and monoclonal antibodies, including binding fragments and single chain versions, are well known in the art.

"Immunoglobulin" refers to a glycoprotein that functions as an antibody. The terms antibody and immunoglobulin may be used interchangeably. Immunoglobulins are found in the blood and tissue fluids, as well as many other body secretions; they take part in an immune response of an organism to bacteria or foreign substances.

MAC capture antibody (or simply capture antibody) may include a variety of antibodies, and is preferably chicken anti-MAC SA IgY. The capture antibody may include polyclonal immunoglobulin "Y" (IgY) produced by immunization of chickens with *Mycobacterium avium* complex (MAC) secreted antigens (SA) and rendered highly specific for MAC SA by absorption with heterologous bacteria (mycobacteria and non-mycobacteria) or antigens from these bacteria. The IgY is harvested from eggs laid by the immunized chickens, purified by standard methods, and absorbed with heterologous bacterial cells or antigens prior to use in the assay as anti-MAC SA IgY.

MAC detection antibody (or simply detection antibody or detector antibody) may include a variety of antibodies, and is preferably rabbit anti-MAC SA IgG. The detection antibody may include polyclonal immunoglobulin "G" (IgG) produced by immunization of rabbits with *Mycobacterium avium* complex (MAC) secreted antigens (SA) and rendered highly specific for MAC SA by absorption with heterologous bacteria (mycobacteria and non-mycobacteria) or antigens from these bacteria. The IgG is harvested from rabbit serum, purified by standard methods, and absorbed with heterologous bacterial cells or antigens prior to use in the assay as anti-MAC SA IgG. It is contemplated that the IgG for the detection antibody could be raised in many mammalian animal species.

"Conjugate" when used herein refers to a detector molecule, such as goat anti-rabbit immunoglobulin-specific antibody, that has been chemically coupled to an indicator system, also called a "label". Other such systems capable of detecting immunoglobulins, such as enzyme-conjugated protein G, can also be used for practicing the present invention. It is also contemplated that the term "conjugate" specifically includes a conjugated antibody against detector (i.e. detection) antibody (see FIGS. 1 and 2).

"Label" when used herein refers to a detectable compound or composition which is conjugated directly or indirectly to an antibody so as to generate a "labeled" antibody (conjugate). The label may be detectable by itself (for example radioisotope label or fluorescent label) or, in the case of an enzymatic label, may catalyze chemical alteration of a substrate compound or composition the product of which is then detectable.

"Subject" refers to any organism classified as a mammal, including humans, domestic and farm animals, and zoo, sports, or pet animals, such as dogs, horses, cats, cattle, pigs, sheep, etc. Preferably, the mammal is human. More preferably, the mammal is bovine.

"Specificity" as used in this application refers to analytical specificity, meaning the ability of the assay to distinguish among similar but not identical analytes as in the secreted antigens of *M. avium* versus secreted antigens of *M. phlei*

"Sensitivity" as used in this application refers to analytical sensitivity, the minimum concentration of analytes detectable by an assay; for example, in the preferred construction the MAC-ELISA can detect 20 ng/mL MAC secreted antigens in a culture.

Detection of antigens specific for MAC bacteria secreted during growth in liquid culture media using antigen-capture ELISA technology is provided. This assay is also referred to as "MAC-ELISA". The assay takes advantage of the abundant cell products made by the pathogen during culture, not solely on the DNA of the organism.

Novel compositions are provided, which include a capture antibody and a detection antibody. The capture antibody may be affixed to solid support, such as a microtiter plate. The capture antibody may be polyclonal or monoclonal. For example, the capture antibody may be polyclonal chicken anti-MAC secreted antigens. The detection antibody may also be polyclonal or monoclonal. For example, the detection antibody may be polyclonal rabbit anti-MAC secreted antigens. Both antibodies can be prepared by immunization of the respective animals with MAC secreted antigens. Preferably, this is followed by removal of non-MAC-specific antibodies by absorption, for example with other bacteria or their antigens.

In one embodiment of the invention, the step-wise MAC-ELISA procedure is conducted as follows: coat a microtiter plate with capture antibody, add sample (liquid culture medium), incubate, wash away unbound antigens, add the detection antibody and wash away unbound antibody, add a conjugate, e.g. enzyme-conjugated goat anti-rabbit IgG, wash away unbound material, add substrate, and measure the resulting color using an ELISA reader. After plate coating (an overnight procedure) the assay typically requires less than 2 hours to complete.

Figure 2:
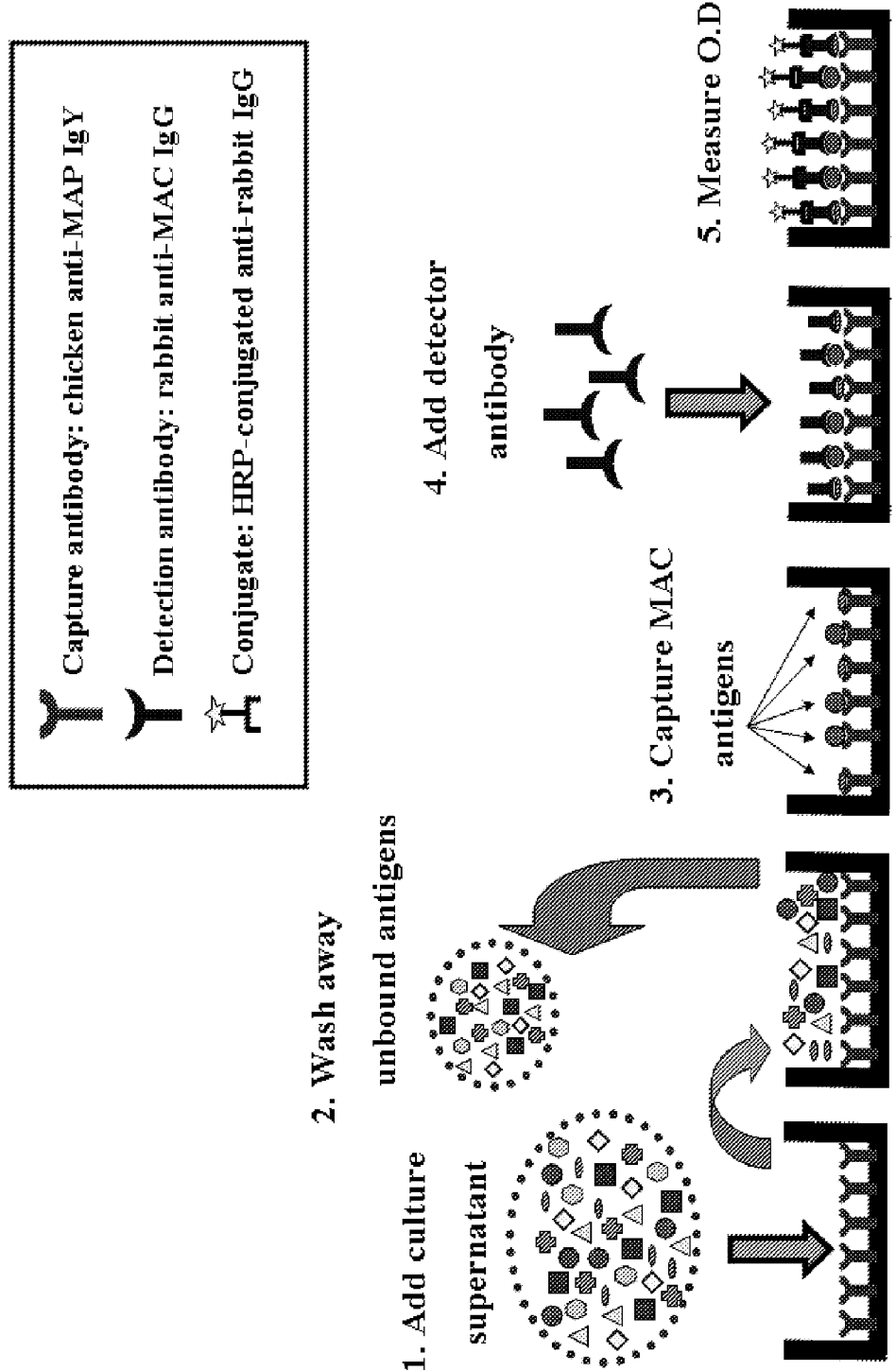
FIG. 2 is a schematic diagram of one embodiment of the MAC-ELISA procedure according to the present invention.

FIGS. 1 and 2 are schematic outlines of the systems and methods according to the present invention. In one example of the assay, shown in FIGS. 1 and 2, there are 4 layers. They are described from the bottom surface (e.g. plastic surface) up. Layer #1 is a capture antibody. This capture antibody can be chicken anti-MAC secreted antigen antibody (IgY) that, prior to use, has been preferably absorbed with heterologous antigens rendering it highly specific for MAC antigens. Layer #2 is MAC secreted antigens from a liquid culture, which antigens bind to the capture antibody. Layer #3 is a detector antibody. In this example, the detector antibody is rabbit anti-MAC secreted antigen antibody (IgG) that, prior to use, has been absorbed with heterologous antigens rendering it highly specific for MAC antigens. In this example, the detector antibody is not labeled, although in some embodiments the detector antibody may be labeled. Layer #4 is a signal system, such as a conjugate (conjugated antibody against detector antibody). The purpose of the signal system is to recognize that the detector antibody has bound in the reaction and trigger a measurable signal. Examples of commercially available suitable conjugates include, for example HRP-conjugated goat anti-rabbit IgG. This is a common way to detect antibody binding, but there are others, some of which are non-antibody based, e.g. they are based on the use of protein G or A.

Some of the advantages of this invention, called MAC-ELISA, include that it is simpler and it saves both time and money relative to current technologies. It also is a novel approach to identification of mycobacteria in culture and could be evaluated for *M. tuberculosis* complex pathogens as well. It eliminates the need for expensive instrument, e.g. BACTEC MGIT 960 (~$50,000 each), and allows cultures to be screened for presence of MAC mycobacteria for relatively small per assay costs. Assay specificity is sufficiently high that no further testing, e.g. PCR, is necessary in many situations when diagnosis of a MAC species is sufficiently precise. In one aspect, the MAC-ELISA triages cultures allowing PCR resources and technician time to be focused only on those cultures with a high likelihood of containing MAC. If desired, follow-up PCR assays can simply confirm the MAC-ELISA diagnosis or determine which member of the MAC is growing in the culture tube, e.g. *M. avium* subspecies *avium*, *M. avium* subspecies *paratuberculosis*, or *M. avium* subspecies *hominissuis*. The MAC-ELISA thus saves laboratory time by triaging culture-positive samples and eliminating the need to perform PCRs on mycobacterial isolates that are not pathogenic (i.e. non-MAC).

In one aspect of the present invention, MAC culture detection based on secreted antigens (SA) common to all MAC is provided. Antigens typically exceed cells by 1,000-fold making better detection targets. Novel antigen-capture antibody is provided. Use of chickens to produce anti-MAC SA IgY is provided. The antigens are used to immunize chickens. Absorption of IgY to make it MAC-specific may be performed. Novel and different detector antibodies are also provided. For example, the use of rabbits to produce anti-MAC SA IgG is contemplated. Antigens may be used to immunize rabbits. Absorption of IgG to make it MAC-specific may be performed. Thus, a relatively low-cost technology for detection of mycobacterial pathogens is provided.

The methods of the present invention can be practiced with a variety of bacterial strains, preferably mycobacterial strains, including but not limited to the *Mycobacterium avium* complex (*Mycobacterium avium* subspecies *avium*, *Mycobacterium avium* subspecies *hominissuis*, *Mycobacterium avium* subspecies *paratuberculosis*, and *Mycobacterium avium* subspecies *sylvaticum*), the *Mycobacterium tuberculosis* complex (MTBC), *Mycobacterium simiae*, etc.

Liquid cultures useful for practicing the invention may be obtained from other mycobacterial strains. Such liquid cultures may be used as antigenic preparations; liquid cultures from two or more bacterial strains may also be combined. Preferably, liquid cultures should be obtained from clinical *M. avium* strains, rather than from laboratory-maintained *M. avium* strains.

To practice this invention, a skilled artisan will know to use other media compositions, broths, etc., suitable for growth of mycobacteria, in order to obtain secreted antigens in liquid cultures. These media may be modified, supplemented with various compounds, acidified, etc. One skilled in the art will know how to optimize the assays by defining the optimal culture incubation time window, and by developing new media to induce antigen secretion. Addition of glycerol enhances bacterial growth and yield of antigens. Preferably, the media should be glycerol-based. Existing commercial media may be modified; for example, 7H9 broth (Becton Dickinson, Cockeysville, Md.) may be modified by replacing the glucose with glycerol. This substitution enhances bacterial growth and results in improved yield of antigens. The pH of the media should preferably be kept at 5.5 to 6.5. More preferably, the pH of the media should be kept at about 6.0. In a preferred embodiment, the media for bacterial growth is modified Watson-Reid (WR) broth (formulation described in Sung and Collins, 2003, *Appl. Environ. Microbiol.* 69: 6833-6840) with a pH of about 6.0.

In one example, the culture of *M. paratuberculosis* in an early-log phase is centrifuged to remove (pellet) the bacteria. The remaining aqueous liquid culture is then concentrated using a size-exclusion filter, preferably a 5,000 molecular weight size-exclusion filter. The liquid culture may also be dialyzed, for example using 10 mM PBS, pH 6.8.

The entire aqueous phase that is obtained from a bacterial culture should be considered a cellular filtrate, synonymous with secreted antigens. For example, if centrifugation of 3,000×g for 10 minutes was used to separate (pellet) the bacteria, then the entire supernatant should be considered liquid culture.

The liquid culture may include a variety of antigenic compounds, such as various mycobacterial proteins, carbohydrates, lipids, metabolites, growth factors, etc. Some of these proteins may, for example, be further modified by phosphorylation, glycosylation, and/or acetylation. The compounds in the liquid culture may be extracellular, secreted, excreted, byproducts of bacterial metabolism, etc. In general, it is only required that the liquid culture includes compounds that act as antigens and that are capable of eliciting the immune response.

In one embodiment, the antibodies are mixed with absorbing antigens prior to contacting them with liquid cultures containing *M. avium* antigens. The absorbing antigens are mixed to absorb the nonspecific antibodies in the sample. The absorbing antigens may be added in the form of an absorbing antigen preparation. These absorbing antigens may be from one type of mycobacteria. Alternatively, they may be from multiple different mycobacteria. Preferably, the absorbing antigens are from *Mycobacterium terrae*, *Mycobacterium phlei*, *E. coli*, or any combinations thereof. The antigens may include cellular extracts of these organisms and in some examples are used at a final concentration of about 250 micrograms per milliliter of diluted sample, the preferred sample dilution being 1:50.

In another embodiment, the invention provides an antibody that specifically binds to any of the above or below described antigens. This is a *M. avium* complex-specific antibody. Optionally, the antibody is a monoclonal antibody, humanized antibody, antibody fragment, or single-chain antibody. The *M. avium*-specific antibody is capable of binding to the antigen, creating an antigen-antibody complex. Examples of antibodies are the capture antibody and the detection antibody.

The antigen-capture antibody complex may be attached to solid support. Once an antigen-capture antibody complex is formed, a second detection antibody or comparable detection molecule is used to detect the presence of the antigen. The detection antibody binds to the antigen. The second antibody is thus used to detect the presence of the MAC antigens bound to the first antibody. The conjugate then detects the presence of the detector antibody and creates a measurable signal such as color reaction measured by an ELISA reader.

As an alternative to the conjugate, the detector antibody itself may be labeled with a label, for example, a bead, a radioisotope, a ligand, a chemiluminescent molecule, a dye, a fluorescent molecule, or an enzyme. Labeled antibodies and reagents useful in immunoassays are disclosed in U.S. Pat. No. 4,490,473.

Radioactive labels such as iodine-125 ($^{125}$I) or other radioactive elements may be applied by known procedures. Techniques for labeling antibodies with $^{125}$I or other radioactive labels are described in Greenwood et al., 1963, *Biochem. J.* 89: 114-123; Harlow and Lane, 2006, *Labeling Antibodies with Iodine*, Cold Spring Harbor Protocols, 2006: pdb-.prot4287.

Fluorescent labels and procedures for coupling them to antibodies are described in U.S. Pat. Nos. 4,256,834 and 4,261,968. Labeled secondary antibody conjugates are known, and may include labeled biotin-binding proteins for detection of biotinylated targets, fluorophore-labeled Protein A and G conjugates, gold conjugates, and the zenon antibody labeling technology (Invitrogen, Carlsbad, Calif.).

A wide variety of enzymatic labels may be applied, and these are selected in conjunction with the substrate to be used in the analysis by procedures well-known in the art. For example, enzymes such as alkaline phosphatase, horseradish peroxidase, catalase, peroxidase, betaglucuronidase, glucose-6-phosphate dehydrogenase, urease, phosphatase, and glucose oxidase are conveniently linked to antibodies by art recognized techniques such as those described in U.S. Pat. Nos. 3,875,011, 3,791,932, and 3,879,262.

Alternatively, the binding of detection antibody may be inferred by the adherence of the complex to a solid surface to which this second antibody is adherent, or by the ability of the complex to activate the complement components in sera, or by other means known in the art.

The assay format may be Western blot, radioimmunoprecipitation, radioimmunoassay (RIA), latex particle agglutination, or an enzyme-linked immunosorbent assay (ELISA), including a sandwich ELISA or lateral-flow ELISA.

The method may employ a solid support such as a column, a dipstick, a filter or a microtiter dish. The ELISA may include detection of an antibody that binds to a *M. avium*-specific antigen using a labeled anti-Ig antibody. The antigen used in the practice of the method may be obtained from *M. avium* complex. Preferably, the antigen may be obtained from liquid culture of *M. avium* complex. The ELISA also may be a competitive assay. The assay may involve quantification. The assay may also be automated, and may, for example, be run on standard ELISA automated plate readers.

In one embodiment, systems for the detection of *M. avium* complex are provided. The systems include antibodies that bind immunologically to *M. avium* complex-specific antigens from a provided sample. The systems may include an antigen obtained from *M. avium* complex liquid culture as a positive control.

The detection antibody may be directly labeled, for example, with a bead, a radioisotope, a ligand, a chemiluminescent molecule, a fluorescent molecule, an enzyme, or with another detectable conjugate. Alternatively, presence of the antigen-bound detection antibody in the assay can be determined by a conjugate such as an antibody-conjugate. The determination of conjugate binding can be quantitative.

In one embodiment, the present invention relates to an ELISA diagnostic kit for the assay of *M. avium* complex antigens in a sample obtained from a liquid culture (MAC-ELISA). A skilled artisan may further improve the signal-to-noise ratio of the diagnostic test by amplifying the signal coming from the label such as using the biotin-avidin labeling method for antibody conjugate signal amplification.

In one embodiment, the kit can contain the already absorbed chicken anti-MAC antibody. Alternatively, the end user can do the absorption step.

Some embodiments of the present invention are described in Shin et al., 2009, *Clinical and Vaccine Immunology* (in press), which is herein incorporated by reference.

EXAMPLES

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

Bacterial Strains, Cultures, and Preparations of Antigens

Bacterial strains used in the experiments included: *Mycobacterium avium* subsp. *paratuberculosis* (MAP): JTC303, DT114, K-10, ATCC19698; other mycobacteria: 62 species including *M. avium* and *M. phlei*; non-mycobacterial spp.: 17 species including *E. coli* and unknown fungus spp.

To develop a MAC-antigen capture ELISA with anti-MAC antibody as the solid phase, a number of organism cultures were prepared. *Mycobacterium avium* complex (MAC) strains were selected to encompass the most clinically important *M. avium* subspecies using both type strains and clinical strains. Antibodies were produced by immunization of rabbits (IgG) and chickens (IgY) with MAP and MAC culture filtrate (CF) antigens. The bacterial strains used for antibody production and tested in this study are listed in Table 1. Briefly, MAP ATCC19698, MAP JTC114, and MAP JTC303 were cultivated in modified Watson-Reid (mWR; pH 6.0) broth media supplemented with 2 µg/ml of Mycobactin J (Allied Monitor, Fayette, Mo.). The static cultivation was performed by inoculating 100 µL of $10^9$ CFU/mL seedlot culture into the cell culture flask (75 cm$^2$ canned neck, Corning INC., NY) containing 50 ml of mWR broth medium for 10 weeks at 37° C. in 5% $CO_2$ humidified conditions.

MAP CF antigens were harvested and pooled as previously described (Shin et al., 2008, *Clin. Vaccine Immunol.* 15: 1277-1281). Strains MAA (ATCC35712) and MAH 104 were cultured in mWR for 6 weeks at 37° C. to obtain and pool MAC antigens.

Cellular extracts (CEAs) were used to remove by absorption cross-reactive antibodies from the rabbit anti-MAC IgG and chicken anti-MAC IgY as previously described (Shin et al., 2008, *Clin. Vaccine Immunol.* 15: 1277-1281). To prepare cellular extract antigens, *Mycobacterium intracellularae* ATCC 13950, *M. intracellularae* ATCC 25122, and *Mycobacterium scrofulaceum* ATCC 19981 were cultivated in mWR broth for 4 weeks 37° C. *Mycobacterium phlei* ATCC 11758 and *Mycobacterium terrae* ATCC 15755 strains were cultivated in mWR for 2 weeks at 37° C.

To evaluate antibody specificity, other non-MAC mycobacterial strains were cultured in 7H9 broth supplemented with 10% OADC (Becton Dickinson, Sparks, Md.) for 2 to 4 weeks at 37° C. (Table 1). Non-mycobacterial strains were grown in Luria-Bertani (LB) broth.

For preparation of cellular antigen extracts from each bacterium grown in mWR, 7H9 or LB broth were prepared as previously described. The antigens included: concentrated liquid culture antigens (CFA); and cellular extract antigens (CEA). The concentration of proteins in each CFA and CEA preparation was determined by BCA protein assay kit (Pierce, Rockford, Ill.).

Antibody Production

MAC (two strains) and MAP (three strains) antigen pools were made to immunize rabbits and chickens. Briefly, 250 µL of culture filtrate antigens from each strain were pooled, mixed, adjusted to a final concentration of 1000 µg/mL and stored as 1 mL aliquots at −20° C. until use. A total of four chickens and four rabbits were used for production of antibody, two each for anti-MAP and anti-MAC.

At each immunization, laying chickens were inoculated with 500 µl of CF antigens mixed with an equal volume of Freund's incomplete adjuvant (FIA). The first immunization was given subcutaneously. Subsequent immunizations were given intramuscularly, the first 2 weeks later, and the remaining four at 1 week intervals. Eggs from each hen were collected daily after the second immunization, labeled, and stored at 4° C. until use.

The IgY was precipitated from egg yolk by adding 1 volume of 40% PEG 8000 (Sigma, Gaithersburg, Md.) in PBS to 3 volumes of egg yolk then centrifuged at 13,000×g for 20 min. The purified IgY was then dialyzed four times with 1 L 10 mM PBS.

Immunization of rabbits for production of rabbit anti-MAP and anti-MAC antibody followed essentially the same protocol as used for chickens with slight modification. Briefly, each rabbit was intradermally inoculated with 500 µg/mL CF antigen pool in an equal volume of FIA. The subsequent three immunizations were done by subcutaneous inoculation of 250 µg/mL CF antigen pool in an equal volume of FIA at 2 week intervals. After the first and third immunizations, the serum antibody levels to each antigen were measured by ELISA. After the fourth immunization serum was harvested from each rabbit. Rabbit IgG purification was then performed using ImmunoPure (G) IgG Purification Kit (Pierce, Rockford, Ill.) following manufacturer's instructions.

Both chicken IgY and rabbit IgG were pure as evidenced by a single band by SDS-PAGE comparable to the commercial antibody controls. The yield was 4-5 mg/mL of IgY from a single egg and 10 mL of 2-3 mg/mL rabbit IgG by BCA assay.

Enhancement of Antibody Specificity

The specificity of rabbit anti-MAP and anti-MAC IgG was enhanced by absorption by both *M. phlei* and *E. coli* antigens; chicken anti-MAP and anti-MAC IgY was enhanced by absorption with *M. phlei* antigens. Briefly, 100 µg of purified IgY was mixed with $10^7$ CFU/mL of *M. phlei* ATCC 11758 and incubated at 4° C. overnight. The mixture was then filtered using a 0.2 µm syringe filter (Nalgene, Rochester, N.Y.). The filtered antibody was dialyzed in 10 mM PBS three times and the final concentration of absorbed anti-MAP and anti-MAC IgY was determined using the BCA protein assay. As intact mycobacterial cells alone were not sufficient for removal of the cross-reactivity of rabbit anti-MAP and anti-MAC IgG with other bacteria, CE antigens of both *M. phlei* ATCC 11758 (500 µg/mL) and *E. coli* DH5α (200 µg/mL) were used to absorb cross-reactive rabbit antibodies. Only absorbed chicken IgY and rabbit IgG were employed in the final assay (referred to as "chicken anti-MAP IgY/anti-MAC IgY" and "rabbit anti-MAP IgG" and "rabbit anti-MAC IgG").

Figure 10:
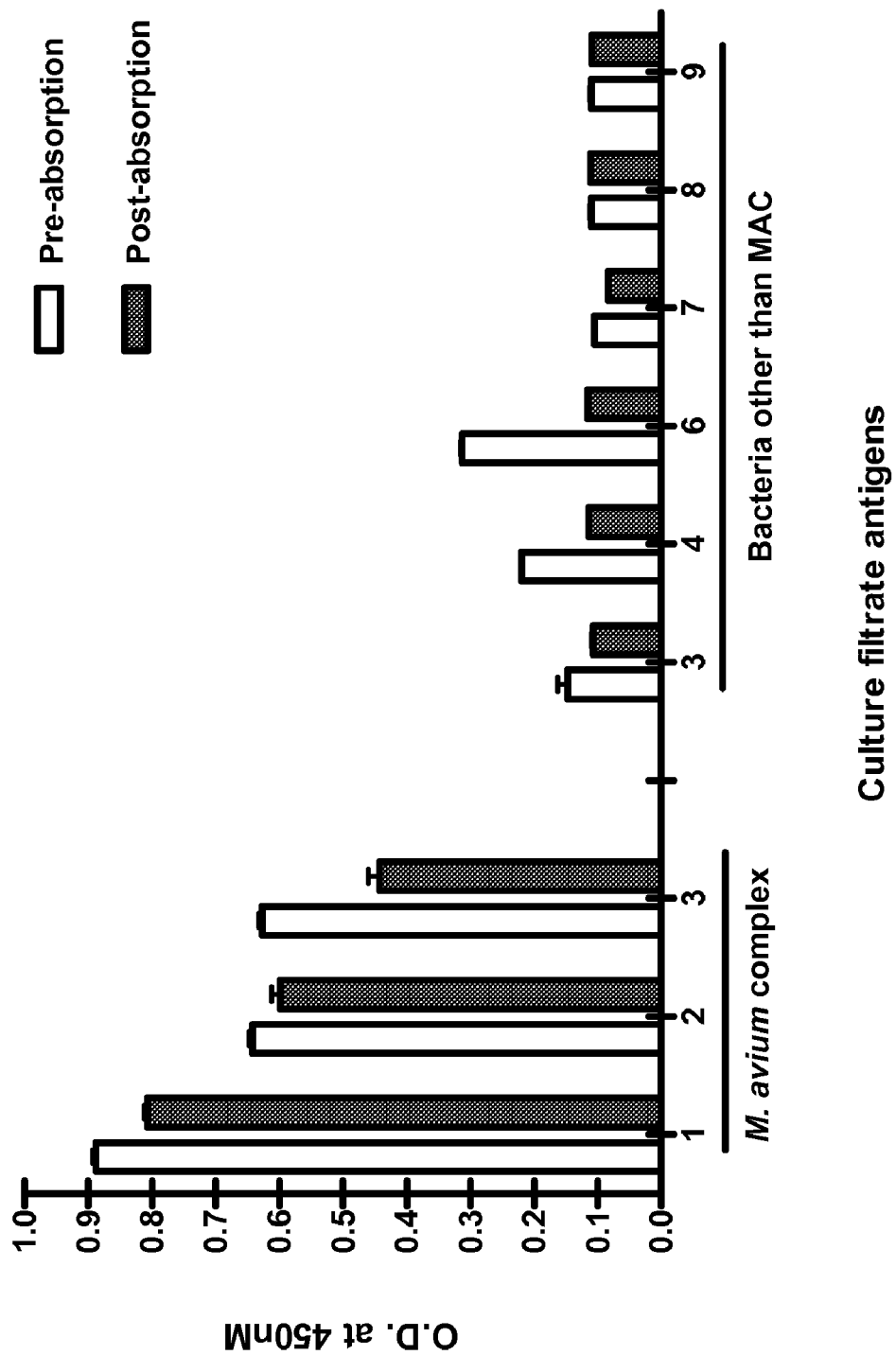
FIG. 10 is a graph depicting comparison of single antibody cross-reactivity pre- and post-absorption, using chicken anti-MAC IgY.

FIG. 10 shows a comparison of single antibody cross-reactivity pre- and post-absorption, using a chicken anti-MAC IgY. The vertical bars indicate: 1: *Mycobacterium avium* subsp. *paratuberculosis* ATCC19968, 2: *Mycobacterium avium* subsp. *avium* ATCC35712, 3: *Mycobacterium* intracellulare ATCC25122, 4: *Mycobacterium phlei* ATCC11758, 5: *Mycobacterium terrae* ATCC15755, 6: *Mycobacterium scrofulaceum* ATCC19981, 7: *Corynebacterium pseudotuberculosis* clinical isolate, 8: *Escherichia coli*/ATCC25922, 9: A mixture of environmental bacteria including *Aeromonas hydrophila, Enterobacter aerogenes, Enterococcus faecalis, Klebsiella pneumonia, Pseudomonas aeruginosa,* and *Proteus vulgaris.*

Figure 11:
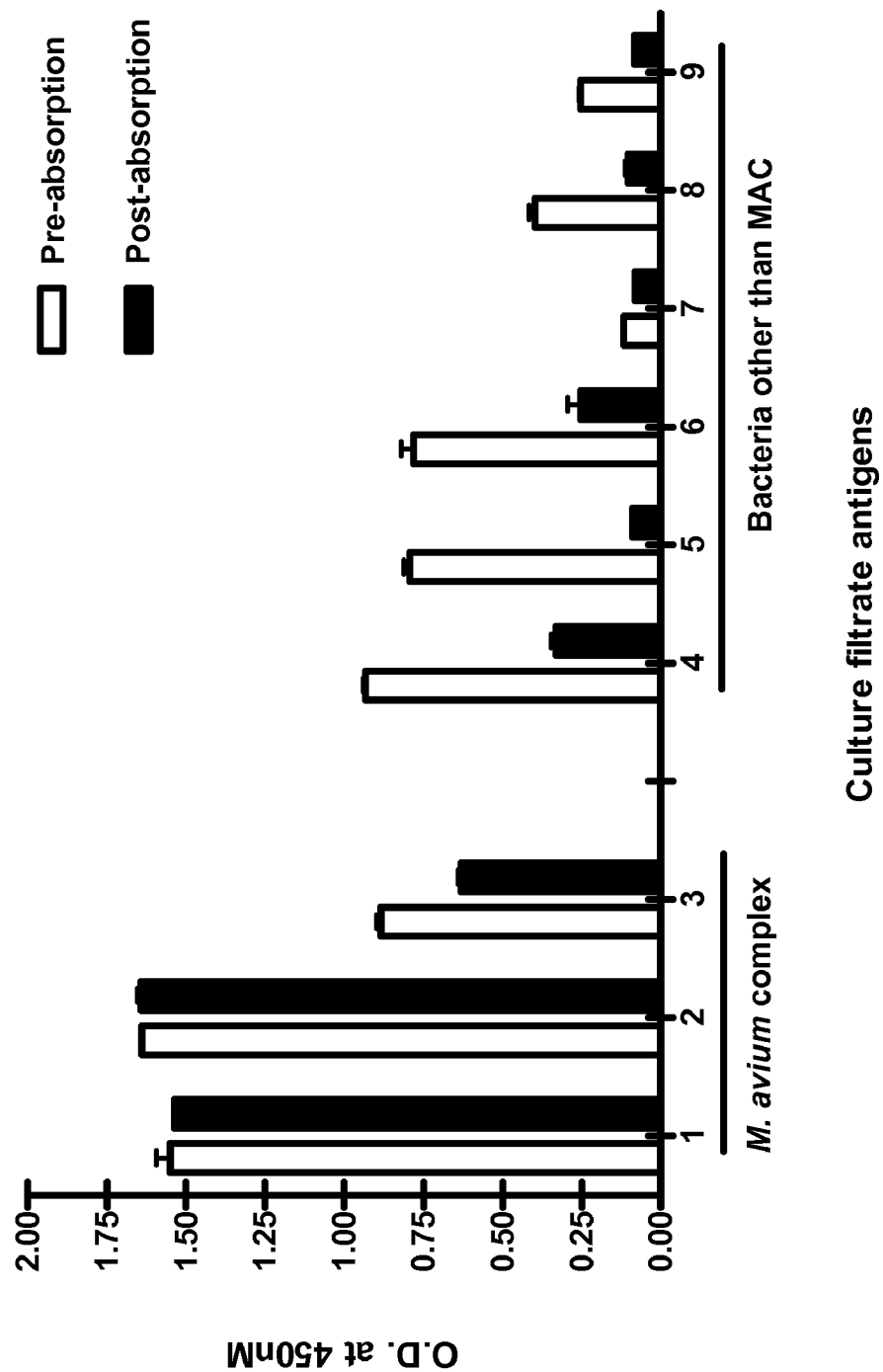
FIG. 11 is a graph depicting comparison of single antibody cross-reactivity pre- and post-absorption, using rabbit anti-MAC IgG.

FIG. 11 shows a comparison of single antibody cross-reactivity pre- and post-absorption, using a rabbit anti-MAC IgG. The vertical bars indicate: 1: *Mycobacterium avium* subsp. *paratuberculosis* ATCC19968, 2: *Mycobacterium avium* subsp. *avium* ATCC35712, 3: *Mycobacterium intracellulare* ATCC25122, 4: *Mycobacterium phlei* ATCC11758, 5: *Mycobacterium terrae* ATCC15755, 6: *Mycobacterium scrofulaceum* ATCC19981, 7: *Corynebacterium pseudotuberculosis* clinical isolate, 8: *Escherichia coli* ATCC25922, 9: A mixture of environmental bacteria including *Aeromonas hydrophila, Enterobacter aerogenes, Enterococcus faecalis, Klebsiella pneumonia, Pseudomonas aeruginosa,* and *Proteus vulgaris.*

Specificity of Anti-MAC Antibody Preparations Before and after Absorption

Reactivity of chicken anti-MAC IgY and rabbit anti-MAC IgG was tested by ELISA both before and after absorption using multiple mycobacterial CFA and CE antigens. Briefly, 2 μg/mL of test antigen was coated on wells of a 96 well plate (Maxisorp®, Nalge Nunc International, Rochester, N.Y.) by overnight incubation at 4° C. After washing three times with wash buffer (KPL, Gaithersburg, Md.), the wells were blocked with 10% normal goat serum (Sigma, St. Louis, Mo.) at room temperature for 2 hrs. Either (a) 100 μL of 2 μg/mL absorbed or non-absorbed anti-MAC IgY or (b) 100 μL of 1:4,000 diluted absorbed or non-absorbed rabbit anti-MAC IgG were added to each well then incubated at RT for 30 min while shaking at 60 rpm. After washing wells five times with wash buffer, HRP-conjugated rabbit anti-IgY (Gentel Biosciences, Madison, Wis.) at a dilution of 1:4,000 or HRP-conjugated sheep anti-rabbit IgG (Vector, Burlingame, Calif.) at a dilution of 1:5,000 was added to each well and incubated for 30 min at RT. Plates were washed five times with wash buffer (KPL, Gaithersburg, Ill.), after which 100 μL of TMB substrate (TMBE-500, Moss Inc., Pasadena, Md.) was added to each well followed by incubation for 1 min at RT. The reaction was then stopped by addition of 100 μL stop solution (KPL, Gaithersburg, Ill.). The optical density (OD) of final reaction in each well was measured at 450 nm using an ELISA reader (μQuant, Bio-Tek instruments Inc., Winooski, Vt.).

Development of MAC-ELISA Protocol

Important reagents in the MAC-ELISA are: 1) the solid phase capture antibody: chicken anti-MAP IgY, 2) the test substance: mycobacterial broth culture fluid potentially containing secreted MAC antigens, 3) the detector antibody: rabbit anti-MAC IgG, and 4) the conjugate: HRP-conjugated goat anti-rabbit IgG (Vector, Burlingame, Calif.) (see, e.g., FIGS. 1 and 2). The concentrations and volumes of the important components were optimized for analytical sensitivity and specificity by reagent titration individually and in various combinations with culture fluid from pure cultures of MAP, MAA, MAH, *M. intracellularae, M. scrofulaceum, M. phlei, M. terrae* and *Corynebacterium pseudotuberculosis*. In one example, the final MAC-ELISA protocol was: Plates (96 well; Maxisorp, Nalge Nunc, Rochester, N.Y.) were first coated with 10 μg of capture antibody, chicken anti-MAC IgY, diluted in coating buffer (KPL, Gaithersburg, Ill.) by overnight incubation at 4° C. After washing three times with wash buffer (KPL, Gaithersburg, Ill.), all wells were blocked with 10% normal goat serum (Sigma, St. Louis, Mo.) at RT for 2 hrs. Fluid (100 μL) from the liquid cultures to be tested was next added to each well. After 1 hr at RT with 60 rpm shaking, the plate was again washed three times with wash buffer. The detector antibody, rabbit anti-MAC IgG (100 μl of 0.5 μg/mL) was added to each well and incubated 30 min at RT. Wells were again washed three times with washing buffer (KPL, Gaithersburg, Ill.). Then, 100 μL of HRP-conjugated goat anti-rabbit IgG (Vector, Burlingame, Calif.) at a dilution of 1:5,000 was added to all wells and incubated for 30 min at RT. Plates then were washed five times with wash buffer (KPL, Gaithersburg, Ill.). Lastly 100 μL TMB substrate (TMBE-500, Moss Inc., Pasadena, Calif.) was added to each well followed by a 1 min RT incubation after which the reaction was stopped by adding 100 μL of stop solution (KPL, Gaithersburg, Ill.) to each well. The optical density (OD) of the final reaction in each well was measured at 450 nm using an ELISA reader (piquant, Bio-Tek instruments Inc., Winooski, Vt.). On each plate there are: two positive controls in duplicate (MAP and MAC culture fluid) and three negative controls (PBS, MGIT medium and *M. phlei* culture fluid). The cutoff value for a positive assay is the mean OD of the two negative control wells plus 0.10.

Analytical Sensitivity and Specificity of the Mac-ELISA

The fluids from pure liquid cultures of both mycobacterial and non-mycobacterial strains were tested. To estimate MAC-ELISA analytical sensitivity, 2-fold serial dilutions of culture fluid (16.0 to 0.0078 μg/mL) from each type strain were tested. Assay results were compared with positive (culture fluid from MAP ATCC19698 and MAA ATCC 35712), and negative (culture fluid from *M. phlei* and *M. terrae*) controls. To determine MAC-ELISA analytical specificity and optimal timing for testing, culture fluid from 7H9 broth cultures of mycobacteria were collected weekly up to 8 weeks (Table 1). Briefly, $10^2$ CFU of each mycobacterial strain was inoculated into 10 mL of Middlebrook 7H9 broth (Difco, Sparks, Md.) supplemented with 0.5% glycerol, and 10% OADC (Middlebrook) and incubated at 37° C. for 8 weeks. For MAP strains, 2 μg/ml of Mycobactin J (Allied Monitor, Fayette, Mo.) also was added to the culture medium for optimal growth. Non-mycobacterial strains were grown in LB medium (Table 1). *Corynebacterium pseudotuberculosis* was grown in brain heart infusion broth. Culture fluid from all strains was tested weekly by MAC-ELISA along with positive and negative controls as described above.

Figure 3:
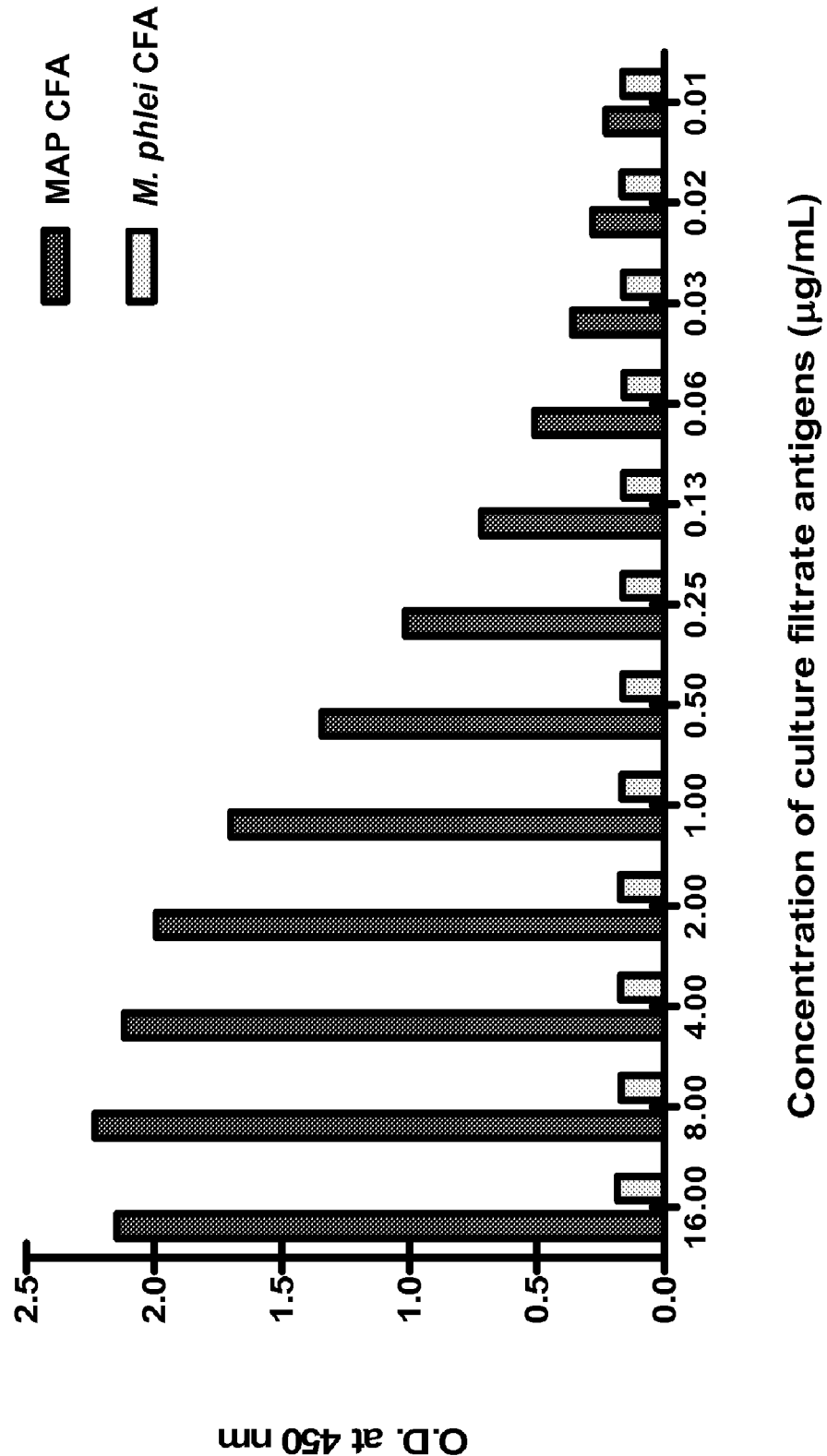
FIG. 3 is a graph showing the analytical sensitivity of the methods according to the present invention, depicting enhanced specificity and sensitivity of the MAC-ELISA by absorption of chicken anti-MAP IGY capture antibody and rabbit anti-MAC IgG detector antibody.
Figure 4:
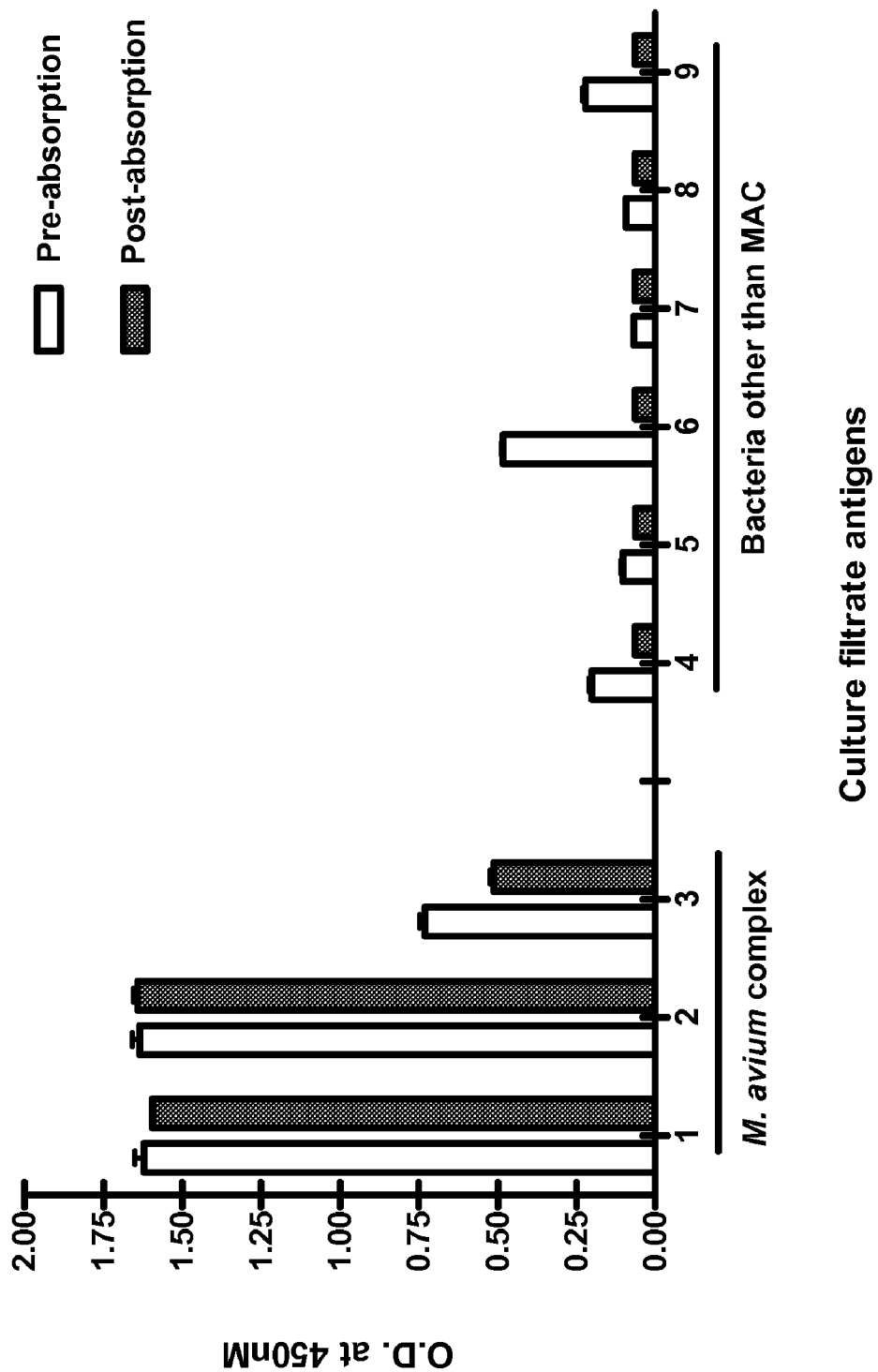
FIG. 4 is a graph showing the analytical detection limit of the MAC-ELISA using purified MAP culture filtrate.
Figure 5:
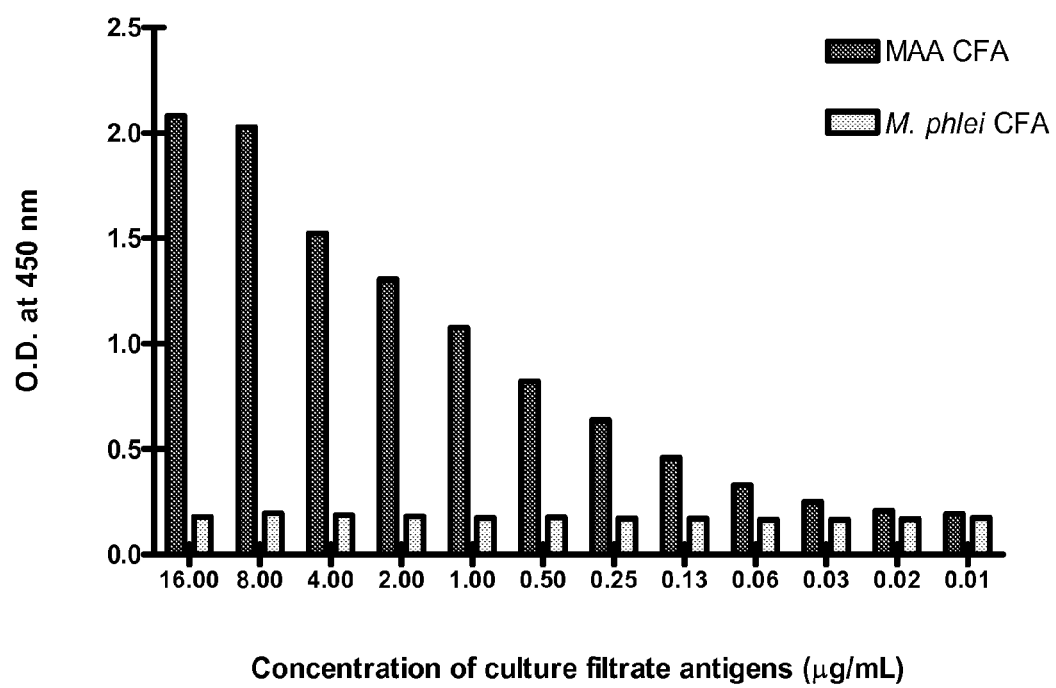
FIG. 5 is a graph showing the analytical detection limit of the MAC-ELISA using purified MAA culture filtrate.

FIGS. 3-5 illustrate the analytical sensitivity of the systems and methods described herein. FIG. 3 shows enhanced specificity and sensitivity of the MAC-ELISA by absorption of chicken anti-MAP IgY capture antibody and rabbit anti-MAC IgG detector antibody. The vertical bars indicate: 1: *Mycobacterium avium* subsp. *paratuberculosis* ATCC19968, 2: *Mycobacterium avium* subsp. *avium* ATCC35712, 3: *Mycobacterium intracellulare* ATCC25122, 4: *Mycobacterium phlei* ATCC11758, 5: *Mycobacterium terrae* ATCC15755, 6: *Mycobacterium scrofulaceum* ATCC19981, 7: *Corynebacterium pseudotuberculosis* clinical isolate, 8: *Escherichia coli* ATCC25922, 9: A mixture of environmental bacteria including *Aeromonas hydrophila, Enterobacter aerogenes, Enterococcus faecalis, Klebsiella pneumonia, Pseudomonas aeruginosa,* and *Proteus vulgaris.*

FIG. 4 shows the analytical detection limit of the MAC-ELISA using purified MAP culture filtrate. The vertical bars indicate: 1: *Mycobacterium avium* subsp. *paratuberculosis* ATCC 19968, 2: *Mycobacterium avium* subsp. *avium* ATCC35712, 3: *Mycobacterium intracellulare* ATCC25122, 4: *Mycobacterium phlei* ATCC11758, 5: *Mycobacterium ter-* rae ATCC15755, 6: *Mycobacterium scrofulaceum* ATCC19981, 7: *Corynebacterium pseudotuberculosis* clinical isolate, 8: *Escherichia coli* ATCC25922, 9: A mixture of environmental bacteria including *Aeromonas hydrophila*, *Enterobacter aerogenes*, *Enterococcus faecalis*, *Klebsiella pneumonia*, *Pseudomonas aeruginosa*, and *Proteus vulgaris*.

FIG. 5 shows the analytical detection limit of the MAC-ELISA using purified MAA culture filtrate. The vertical bars indicate: 1: *Mycobacterium avium* subsp. *paratuberculosis* ATCC 19968, 2: *Mycobacterium avium* subsp. *avium* ATCC35712, 3: *Mycobacterium intracellulare* ATCC25122, 4: *Mycobacterium phlei* ATCC11758, 5: *Mycobacterium terrae* ATCC15755, 6: *Mycobacterium scrofulaceum* ATCC19981, 7: *Corynebacterium pseudotuberculosis* clinical isolate, 8: *Escherichia coli* ATCC25922, 9: A mixture of environmental bacteria including *Aeromonas hydrophila*, *Enterobacter aerogenes*, *Enterococcus faecalis*, *Klebsiella pneumonia*, *Pseudomonas aeruginosa*, and *Proteus vulgaris*.

TABLE 1

Bacterial strains used to assess the specificity of the MAC-ELISA

| Species | Total No. of strains | Reference strain IDs included in total tested | Source other than ATCC[1] | Detection time in MAC-ELISA[2] (weeks) |
|---|---|---|---|---|
| Mycobacterial spp. | | | | |
| *M. avium* subsp. *paratuberculosis* | 13 | ATCC[3]19698, K-10 | JTC[4] | 3 |
| *M. avium* subsp. *avium* | 4 | ATCC35712, ATCC25291 | JTC | 1-2 |
| *M. avium* subsp. *hominissuis* | 6 | 104 | JTC, EPA[5], WSLH[6] | 1-2 |
| *M. intracellulare* | 9 | ATCC13950, ATCC25122 | JTC, EPA, WSLH | 1 |
| *M. silvaticum* | 1 | ATCC49884 | | 3 |
| *M. abscess* | 1 | ATCC19977 | | N |
| *M. asiaticum* | 4 | ATCC25276 | JTC | N |
| *M. bovis* | 3 | ATCC19210 | JTC | N |
| *M. celatum* | 4 | ATCC51130 | JTC | N |
| *M. flavescens* | 2 | ATCC14474 | JTC | N |
| *M. fortuitum* | 2 | ATCC49404 | WSLH | N |
| *M. gordonae* | 2 | ATCC14470 | JTC | N |
| *M. kansasii* | 3 | ATCC12478 | JTC | N |
| *M. lentiflavum* | 2 | ATCC51985 | WSLH | N |
| *M. malmoense* | 1 | ATCC29571 | | N |
| *M. marium* | 2 | ATCC927 | WSLH | N |
| *M. nonchromogenicum* | 1 | ATCC19530 | | N |
| *M. phlei* | 1 | ATCC11758 | | N |
| *M. scrofulaceum* | 7 | ATCC19981 | JTC | N |
| *M. simiae* | 2 | ATCC25275 | WSLH | N |
| *M. smegmatis* | 2 | ATCC14468, mc$^2$155 | | N |
| *M. terrae* | 3 | ATCC15755 | JTC | N |
| Non-mycobacterial spp. | | | | |
| *Aeromonas hydrophlia* | 1 | | WSLH | N |
| *Corynebacterium pseudotuberculosis* | 1 | | JTC | N |
| *Enterococcus faecalis* | 1 | ATCC29212 | WSLH | N |
| *Enterobacter aerogenes* | 1 | | WSLH | N |
| *Escherichia coli* | 4 | ATCC25922 | WSLH | N |
| *Klebsiella pneumonia* | 1 | | WSLH | N |
| *Proteus vulgaris* | 1 | | WSLH | N |
| *Pseudomonas aeruginosa* | 1 | | WSLH | N |
| Unidentified fungi | 6 | | JTC | N |
| Total | 92 | | | |

[1]Isolates were identified using mutiplex PCR and HPLC.
[2]The time in weeks until antigens secreted by MAC bacteria were detected in culture fluid by the MAC-ELISA when $10^2$ CFU of all strains were inoculated into 7H9 broth. N indicates the assay was never positive up to the end of incubation at 8 weeks.
[3]American Type Culture Collection, Manassas, VA
[4]Johne's Testing Center, Madison, WI
[5]Environmental Protection Agency, Cincinnati, OH
[6]Wisconsin State Laboratory of Hygiene, Madison, WI Assessment of MAC-ELISA vs. MGIT960 ParaTB™ Culture System for Pure Cultures Duplicate tubes of MGIT ParaTB Medium™ (Becton Dickinson) were inoculated with serial dilutions of MAP ATCC19698, MAA ATCC 35712, *M. phlei* ATCC 11758, or *M. terrae* ATCC 15755. Briefly, undiluted stock cell suspension (1.0 mL) was added to 9.0 ml of 10 mM PBS (pH 7.2) and 10-fold serial dilutions were made in 10 mM PBS (pH 7.2) with vortexing between each dilution step resulting in 100 to $10^7$ CFU/mL of each of the four mycobacterial strains. From each dilution 100 µL was inoculated into MGIT ParaTB Medium™ (Becton Dickinson, Sparks, Md.). Each MGIT tube contained 7 ml of modified Middlebrook 7H9 broth base with mycobactin J and fluorescent indicator measuring changes in oxygen concentration embedded in silicone on the bottom of the tube. The MGIT ParaTB Medium™ was supplemented as per manufacturer's instructions and incubated at 37° C. in a MGIT 960 instrument.

Tubes were removed when the machine signaled them as positive based on changes in the indicator. For each MGIT-positive tube, culture fluid (100 µL) was then tested by MAC-ELISA with results analyzed in relationship to the Time To Detection (TTD; incubation time in days until signal-positive) for each culture.

Assessment of the MAC-ELISA Using Well-Defined Clinical Cultures

A total of 1,275 animal feces, tissues, water, and soil samples yielding acid-fast stain positive organisms were tested using the MAC-ELISA. This set was obtained from 684 clinical cultures in modified BACTEC 12B medium and 591 clinical cultures in MGIT ParaTB Medium™. Once an instrument signaled positive, acid-fast staining was done on the cultures and contamination was checked by inoculation to 5% sheep blood agar plates. Final identification of mycobacterial isolates was done using as a reference method a multiplex PCR simultaneously targeting mycobacterial 16sDNA and four insertion elements IS900, IS901, IS1311, and IS1245 (Johne's Testing Center, Madison, Wis.) with reference strains as controls. Ultimately these 1,275 clinical samples yielded 340 MAC and 344 non-MAC mycobacteria from modified BACTEC 12B medium and 305 MAC and 286 mycobacteria other than MAC from MGIT ParaTB Medium™. The optimal cutoff, sensitivity, and specificity of the MAC-ELISA were determined by ROC curve analysis.

Validation of the MAC-ELISA to Triage MGIT Signal-Positive Cultures

Prospectively, 652 consecutive clinical samples (animal feces, tissues, water or soil) were processed for MAP isolation following manufacturer's recommendations using the MGIT ParaTB Medium™. The first time the MGIT 960 instrument signaled a tube as "positive" it was removed from the instrument, vortexed and reinserted in the machine. After the tube signaled positive a second time (or if it signaled positive within one week of the 49 day incubation protocol), the MAC-ELISA was performed. For MAC-ELISA negative cultures, acid-fast staining (Ziehl-Neelsen) on culture fluid smears independently assessed the presence of mycobacteria.

The multiplex PCR was used to verify the identity of mycobacteria in all acid-fast stain positive and MAC-ELISA positive MGIT cultures. In all cases of discrepancy between MAC-ELISA and multiplex PCR results, two assays were use to clarify the true identity of mycobacterial isolates: IS900 nested PCR for MAP (greater analytical sensitivity than the multiplex) and HPLC of cell wall mycolic acids for all other mycobacteria (Wisconsin State Laboratory of Hygiene, Madison, Wis.) (Glickman et al., 1994, *J. Clin. Microbiol.* 32: 740-745).

Statistical Analysis

Specificity and sensitivity were evaluated by receiver-operator characteristic (ROC) curves. MAC-ELISA OD values before and after antibody absorption were compared by the t-test. Differences in OD values between MAC cultures and cultures with mycobacteria other than MAC were compared by the Mann-Whitney test. Statistical analyses were done using statistical software (GraphPad Prism version 4.03 for Windows, GraphPad Software, San Diego Calif. USA).

Anti-MAC Antibody Specificity

Prior to absorption with heterologous antigens both chicken anti-MAP and anti-MAC IgY showed cross-reactivity to other mycobacteria such as *M. scrofulaceum, M. phlei* and *M. terrae*. After absorption with *M. phlei* cells, the cross-reactivity to those mycobacteria disappeared without significant decrease in reactivity (ELISA OD) to target MAP and MAC mycobacteria (FIG. 1A). Rabbit anti-MAC and anti-MAP IgG both cross-reacted with non-mycobacteria as well as all mycobacteria tested. After absorption with the CE antigens from *M. phlei* and *E. coli*, however, this cross-reactivity decreased significantly without appreciable change in reactivity to secreted antigens of MAP or MAC (FIG. 1B). The absorbed chicken and rabbit anti-MAC and anti-MAP retained strong reactivity to both MAC and MAP and moderate reactivity to *M. intracellularae*.

Development of MAC-Enzyme Linked Immunosorbent Assay

Numerous combinations and concentrations of chicken and rabbit anti-MAP and anti-MAC were tested during development of the MAC-ELISA. The combination providing optimal sensitivity and specificity for detection of secreted MAC antigens in liquid cultures required use of chicken anti-MAP IgY for antigen-capture and rabbit anti-MAC IgG for captured-antigen detection, together with a suitable commercial conjugate to detect rabbit antibody binding (data not shown) (FIG. 2). Although the antibodies were produced using selected subspecies of MAC, they did not discriminate among MAC subspecies nor between *M. avium* and *M. intracellularae*. The final assay is thus complex-specific, but not species- or subspecies-specific and therefore is referred to as the MAC-ELISA.

MAC-ELISA Specificity and Sensitivity for Pure Cultures

Culture fluid obtained weekly from 92 mycobacterial and non-mycobacterial strains were tested. After 8 weeks of incubation no mycobacteria outside the MAC triggered a positive MAC-ELISA (Table 1). All MAC members (13 MAP, 4 MAA, 6 MAH, 1 MAS, and 9 *M. intracellularae*) became MAC-ELISA positive between 1 and 4 weeks of incubation in Middlebrook 7H9 when the starting inoculum was $10^2$ CFU.

The specificity and sensitivity of MAC-ELISA was enhanced by use of absorbed antibodies (FIGS. 3-5). Assay accuracy using anti-MAP IgY for antigen capture and anti-MAC IgG for antigen detection was superior to all other antibody combinations. The MAC-ELISA analytical sensitivity was 0.03125 μg/mL MAP CFA (FIG. 4) and 0.0625 μg/mL MAA CFA (FIG. 5) when the mean negative control ODs plus 0.10 was used as the cutoff for a positive test.

Optimal Incubation Time for Detection and Detection Limit

Time To Detection (TTD) as reported by the MGIT 960 instrument or incubation time to positive MAC-ELISA were similar, given that the MGIT instrument read cultures hourly and culture fluid was only tested by MAC-ELISA weekly. The MAC-ELISA detection limit for MAP and MAC was $10^1$ CFU/mL. Culture fluid from *M. phlei* never triggered a positive MAC-ELISA (Table 2).

TABLE 2

Comparison of time to positive in days between MAC-ELISA and MGIT cultures

| Inoculum CFU/mL | MAP JTC303 | | MAA ATCC35712 | | *M. phlei* ATCC11758 | |
|---|---|---|---|---|---|---|
| | MGIT TTD[1] | MAC-ELISA[2] | MGIT TTD | MAC-ELISA | MGIT TTD | MAC-ELISA |
| $10^6$-$10^7$ | 4.8 | 7 | 3.5 | 7 | 0.7 | ND[3] |
| $10^5$-$10^6$ | 7.2 | 7 | 5.3 | 7 | 2.6 | ND |
| $10^4$-$10^5$ | 10.1 | 14 | 6.9 | 7 | 4.3 | ND |
| $10^3$-$10^4$ | 12.8 | 21 | 8.7 | 14 | 6.0 | ND |
| $10^2$-$10^3$ | 17.1 | 21 | 10.6 | 14 | 10.4 | ND |
| $10^1$-$10^2$ | 21.5 | 28 | 12.7 | 21 | 14.8 | ND |
| $10^0$-$10^1$ | 39.1 | 35 | 15.8 | 21 | ND | ND |
| $10^{-1}$-$10^0$ | ND | ND | ND | ND | ND | ND |

[1]The MGIT 960 instrument measures fluorescence as an indication of microbial growth hourly.
[2]Culture fluid was tested by MAC-ELISA weekly.
[3]Not detectable in MAC-ELISA up to 56 days of incubation.

ROC Analysis of the MAC-ELISA Using Well-Defined Clinical Cultures

Figure 6:
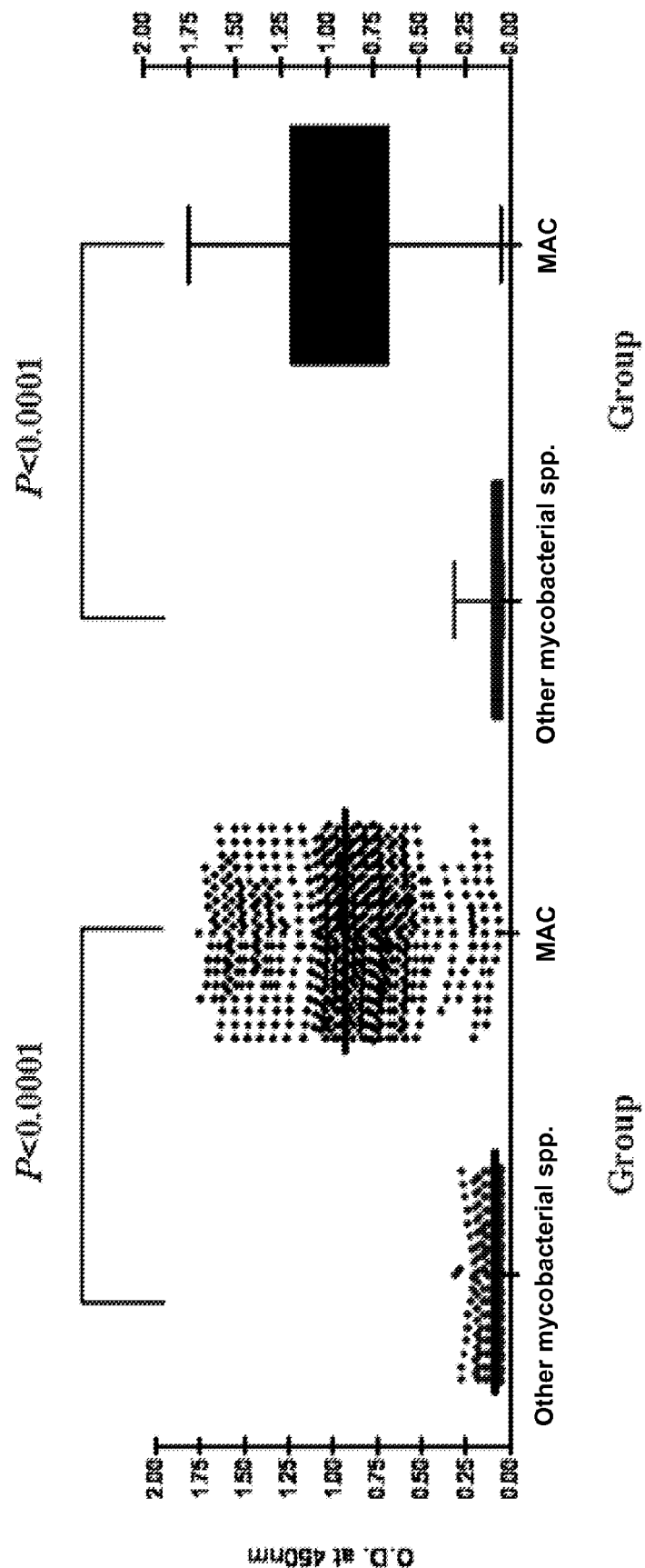
FIG. 6 is a graph showing assessment of the MAC-ELISA on 1,275 well-defined clinical cultures, as a scatter plot of MAC-ELISA OD values for MAC and mycobacteria other than MAC.
Figure 7:
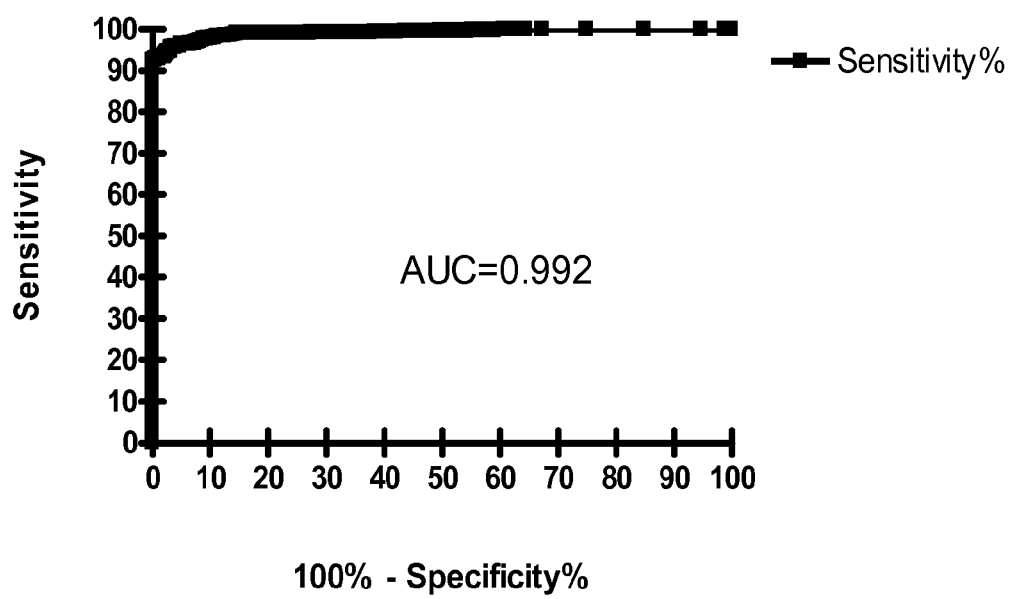
FIG. 7 is a graph showing ROC analysis of the scatter plot data depicted in FIG. 6.

A significant difference in MAC-ELISA OD values was observed between clinical cultures containing MAC versus non-MAC mycobacteria (P<0.0001) (FIG. 6). The cut-off value for maximum assay accuracy was determined by ROC curve analysis. The assay sensitivity and specificity were 92.6% (95% Cl, 90.3-94.5) and 99.9% (95% Cl, 99.2-100), respectively with an area under the ROC curve (AUC) of 0.992 (FIG. 7).

Clinical Application of MAC-ELISA

Figure 8:
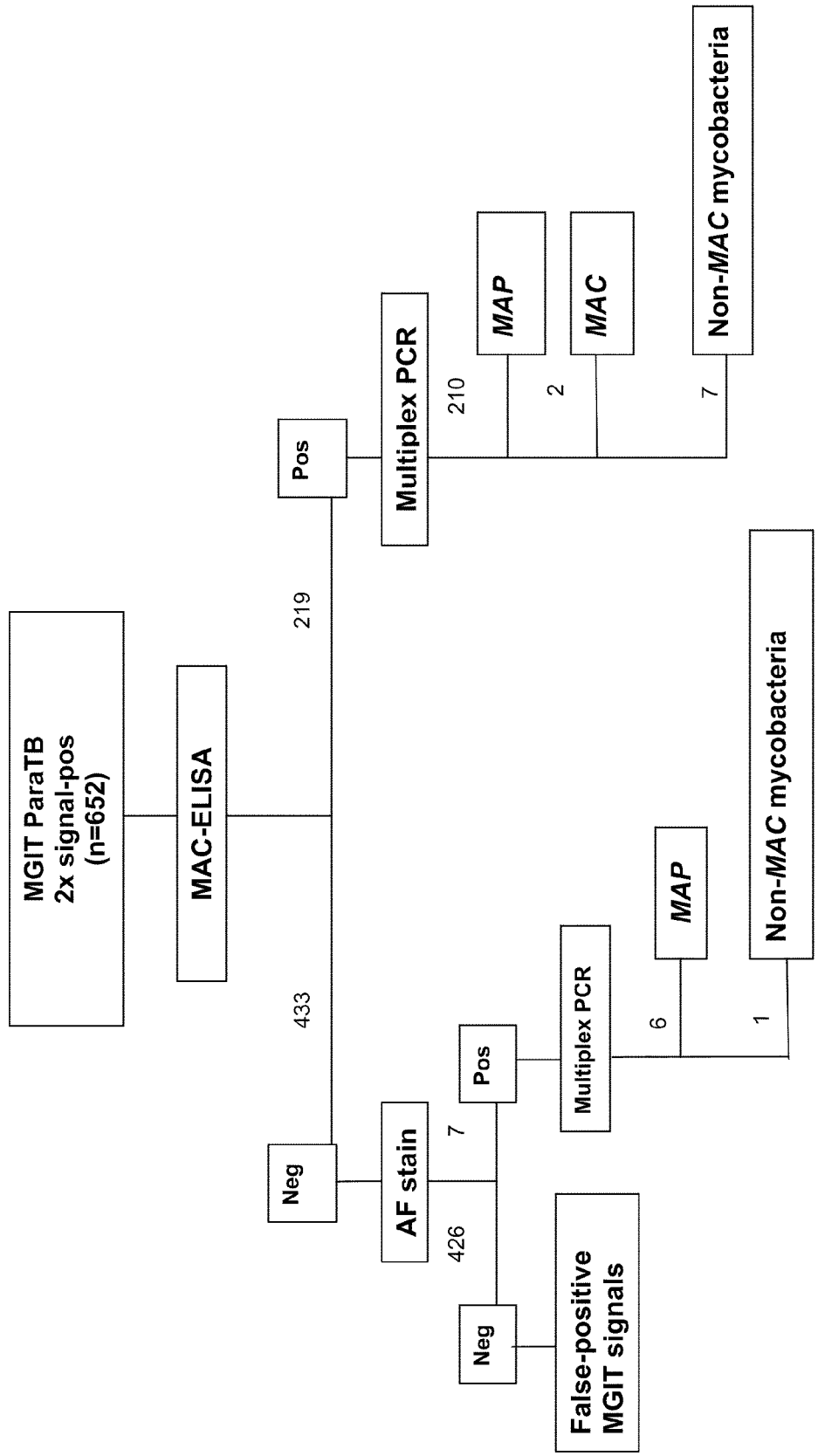
FIG. 8 illustrates clinical application of the MAC-ELISA in conjunction with the MGIT ParaTB Medium™ and MGIT 960 instrument.
Figure 9:
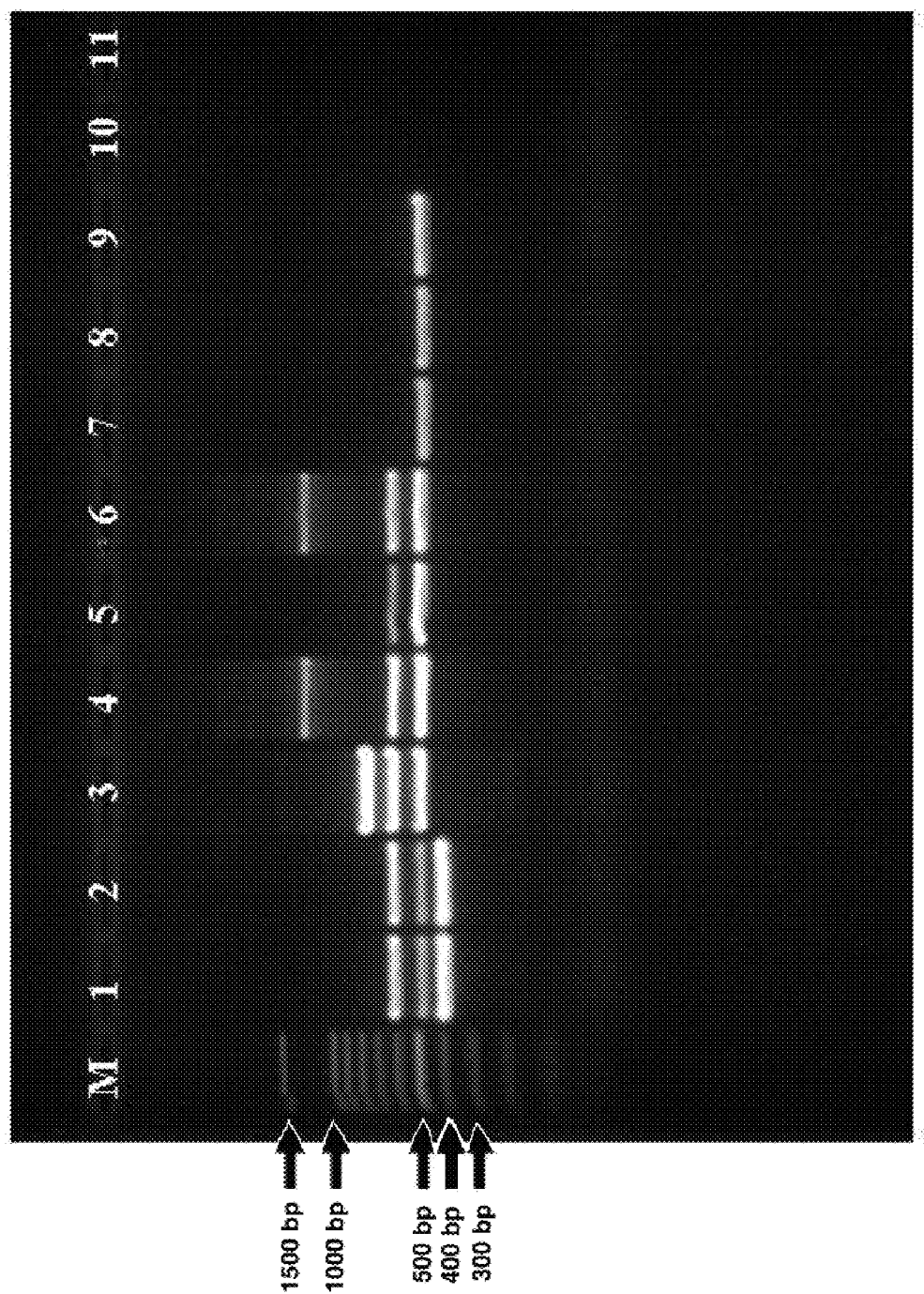
FIG. 9 shows representative data of multiplex PCR. M: Marker, 1: *M. paratuberculosis* ATCC19698, 2: *M. paratuberculosis* human isolate UCF-5, 3: *M. avium* ATCC35712, 4: *M. avium* human isolate 104, 5: *M. intracellulare* ATCC13950, 6: MAC clinical isolate, 7: *M. terrae* ATCC15755, *M. asiaticum* ATCC25274, 9: *M. scrofulaceum* ATCC19981, 10: *E. coli*/DH5α, 11: Negative control.

The MGIT 960 instrument signaled growth in 652 clinical cultures; MAC-ELISA indicated that MAC species were present in 219 (33.6%) of them. Among these 219 cultures, 212 were confirmed as containing MAC organisms (97.8%; 210 MAP and 2 MAC). The other seven were found to contain mycobacteria other than MAC for a false-positive MAC-ELISA rate of 3.2% (7/219) (FIG. 8).

The remaining 433 MGIT-positive cultures were MAC-ELISA-negative (66.4%). Of these, 426 (98.4%) did not contain acid-fast bacteria suggesting a high rate of false-positive signals by the MGIT system. Seven of the 433 MGIT-positive but MAC-ELISA-negative cultures (1.6%) had acid-fast bacteria identified as MAP (n=6) or non-MAC mycobacteria (n=1); a false-negative rate of 6/433 (1.4%) (FIG. 8). More than 500 MGIT signal-negative cultures as well as uninoculated culture medium were also MAC-ELISA negative (data not shown).

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of diagnostic assays and microbiology, are within the scope of this invention. All publications, patents, and patent applications cited herein are incorporated by reference in their entirety for all purposes.

What is claimed is:

1. A method of detecting the presence of a mycobacterium in a liquid culture suitable for growth of mycobacteria, wherein the mycobacterium is a member of the *Mycobacterium avium* complex, comprising the steps of:
   providing a capture antibody obtained from a subject immunized with a the *Mycobacterium avium* complex-secreted antigen;
   contacting the liquid culture with the capture antibody;
   providing a detection antibody obtained from a subject immunized with the *Mycobacterium avium* complex-secreted antigen; and
   detecting the presence of an antigen-bound detection antibody in the liquid culture to indicate the presence of the mycobacterium in the liquid culture.

2. The method of claim 1 further comprising absorbing nonspecific antigens using heterologous antibodies, wherein absorbing is performed prior to contacting the capture antibody and the detection antibody with the liquid culture.

3. The method of claim 2 wherein absorbing nonspecific antigens using heterologous antibodies is performed using heterologous antibodies from *M. phlei* or *E. coli*.

4. The method of claim 1 wherein detecting the presence of an antigen-bound detection antibody in the liquid culture comprises using an enzyme-linked immunosorbent assay.

5. The method of claim 1 wherein the liquid culture is contacted with a capture antibody that is affixed to solid support.

6. The method of claim 1 wherein the liquid culture is contacted with a capture antibody that is a chicken anti-*Mycobacterium avium* complex antibody, and wherein the detection antibody is a rabbit anti-*Mycobacterium avium* complex antibody.

7. The method of claim 1 wherein the detection of the presence of an antigen-bound detection antibody is performed with a detection antibody that is labeled.

8. The method of claim 1 wherein the detection of the presence of an antigen-bound detection antibody is performed with a detection antibody that is conjugated to an enzyme.

9. The method of claim 1 wherein the capture antibody is a chicken anti-*Mycobacterium avium* complex IgY antibody.

* * * * *